United States Patent [19]

Cragoe, Jr. et al.

[11] 4,260,771

[45] Apr. 7, 1981

[54] INTERPHENYLENE 9-THIA-11-OXO-12-AZAPROSTANOIC ACID COMPOUNDS

[75] Inventors: Edward J. Cragoe, Jr.; Ta-Jyh Lee; John B. Bicking, all of Lansdale, Pa.

[73] Assignee: Merck & Co., Inc., Rahway, N.J.

[21] Appl. No.: 105,487

[22] Filed: Dec. 20, 1979

Related U.S. Application Data

[63] Continuation of Ser. No. 965,641, Dec. 1, 1978, abandoned, which is a continuation of Ser. No. 846,065, Oct. 27, 1977, abandoned.

[51] Int. Cl.$^3$ .......................................... C07D 277/04
[52] U.S. Cl. .................................. 548/187; 548/186; 424/270
[58] Field of Search ................ 548/186, 187; 424/270

[56] References Cited

U.S. PATENT DOCUMENTS

| | | | |
|---|---|---|---|
| 4,059,587 | 11/1977 | Smith et al. | 548/187 |
| 4,102,888 | 7/1978 | Smith et al. | 548/187 |

*Primary Examiner*—Nicholas S. Rizzo
*Attorney, Agent, or Firm*—Thomas E. Arther; Mario A. Monaco

[57] ABSTRACT

This invention relates to novel interphenylene 9-thia-11-oxo-12-azaprostanoic acid compounds, salts, and derivatives thereof. These compounds have prostaglandin-like biological activity and are particularly useful as renal vasodilators, as platelet aggregation inhibitors, and for the treatment of certain autoimmune diseases.

7 Claims, No Drawings

INTERPHENYLENE 9-THIA-11-OXO-12-AZAPROSTANOIC ACID COMPOUNDS

This is a continuation of application Ser. No. 965,641, filed Dec. 1, 1978; which in turn is a continuation of U.S. Ser. No. 846,065 filed Oct. 27, 1977, now abandoned.

SUMMARY OF THE INVENTION

This invention relates to novel interphenylene 9-thia-11-oxo-12-azaprostanoic acids, salts, and derivatives which are represented by the following formula:

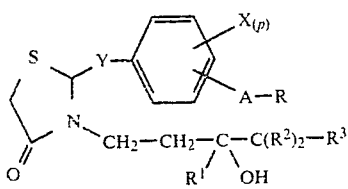

wherein R is selected from the group consisting of carboxy and a carboxy salt which incorporates a pharmaceutically acceptable cation, such as metal cations derived from alkali metals, alkaline earth metals, and amines such as ammonia, primary and secondary amines and quarternary ammonium hydroxides. Especially preferred metal cations are those derived from alkali metals, e.g. sodium, potassium, lithium, and the like, and alkaline earth metals, e.g. calcium, magnesium, and the like and other metals, i.e. aluminum, iron, and zinc.

Pharmaceutically acceptable cations derived from primary, secondary, or tertiary amines, or quaternary ammonium hydroxides are methylamine, dimethylamine, 1-methylpiperazine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium, and the like.

R is also selected from the group alkoxycarbonyl (—$COOR^4$ wherein $R^4$ is alkyl having 1–10 carbon atoms).

A is selected from a group consisting of vinylene, CH=CH, or $(CH_2)_m$ where m is selected from 0 or 2.

Y is selected from the group consisting of —$CH_2CH$=$CH$— or $(CH_2)_{m_1}$ where $m_1$ is 1, 3, or 4.

The groups A-R and Y are located meta or para to each other on the benzene ring.

The sum of carbon atoms in A and Y is 3 or 4.

$X_{(p)}$ is selected from the group consisting of hydrogen, halogen, or lower alkyl, preferably methyl. The point of attachment of group(s) X is either ortho and/or meta to the chain A-R.

p is 1 or 2.

$R^1$ and $R^2$ are independently selected from the group consisting of hydrogen and methyl, $R^3$ is selected from the group consisting of 3-butenyl and 4,4,4-trifluorobutyl, lower alkyl of 3–6 carbon atoms, either straight or branched (e.g., propyl, butyl, amyl, isoamyl, hexyl, 3,3-dimethylbutyl), and lower alkoxy, $OR^5$ where $R^5$ is selected from the group consisting of lower alkyl of 2–5 carbon atoms, straight or branched (e.g., ethyl, propyl, butyl, hexyl, isobutyl, and 3,3,3-trifluoropropyl).

When $R^3$ is lower alkyl and $R^1$ is methyl, they may be joined together to form a polymethylene chain of from 4–7 carbon atoms included in a carbocyclic ring with from 6 to 9 members.

Likewise, when $R^3$ is lower alkyl and $R^1$ is hydrogen, $R^3$ may be joined to the carbon atom bearing $R^1$ and OH to form a polymethylene chain of from 3 to 6 carbon atoms included in a carbocyclic ring with from 5 to 8 members.

It is to be noted that the carbon atom attached to both sulfur and nitrogen and, in certain compounds, the carbon atom bearing the hydroxyl group are asymmetric. This invention also includes the stereoisomers in which these asymmetric centers are exclusively in either one of the two possible configurations, R and S.

BACKGROUND OF THE INVENTION

The compounds of formula I are described as interphenylene 9-thia-11-oxo-12-azaprostanoic acids and derivatives as a means of describing the structural relationship to prostanoic acid, which has the carbon skeleton of the natural prostaglandins as shown in the following formula:

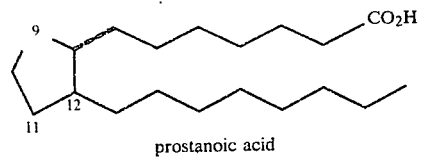

prostanoic acid

The prostaglandins constitute a class of highly functionalized $C_{20}$ fatty acids. They have been shown to occur extensively in low concentrations in mammalian tissues where they are both rapidly anabolized and catabolized and to exhibit a broad spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, FORTSCHR. CHEM. ORG. NATURST., 28, 313 (1970) and G. F. Bundy, A. REP. IN MED. CHEM., 7, 157 (1972)]; biochemistry [J. W. Hinman, A. REV. BIOCHEM., 41, 161 (1972)]; pharmacology [J. R. Weeks, A. REV. PHARM., 12, 317 (1972)]; physiological significance [E. W. Horton, PHYSIOL. REV. 49, 122 (1969)]; and general clinical application [J. E. Hinman, POSTGRAD. MED. J. 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and consequently, the availability is quite restricted.

Our interest has, therefore, been to synthesize novel compounds structurally related to the natural prostaglandins, but with the following unique advantages: (a) simplicity of synthesis leading to low cost of production; (b) specificity of biological activity; and (c) enhanced metabolic stability so that activity can be obtained on oral as well as parenteral administration.

These advantages have been realized in the compounds of this invention. Certain of the compounds exhibit renal vasodilatory activity on oral administration and, therefore, are useful for the treatment of patients with renal impairment. Included in this group are patients with hypertension, renal failure, congestive heart failure, glomerulonephritis, uremia, and chronic renal insufficiency. The compounds of this invention by virtue of their renal vasodilatory activity improve renal function both when used alone or in conjunction with other renal agents. An example of a compound with high renal vasodilatory activity is 4-{3-[3-[2-(1-hydroxycyclohexyl)ethyl]-4-oxo-2-thiazolidinyl]propyl}benzoic acid.

In addition to their activity as renal vasodilators, many compounds of this invention have useful adjunctive properties which give them added utility for the treatment of renal disease. Such properties include diuretic, saluretic, antihypertensive, and immunoregulant activities.

With regard to the indications that the compounds of this invention can be useful in therapy as regulators of the immune response, it can be stated that the basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reactions is involved. Such diseases range from contact dermatitis to such chronic destructive diseases as rheumatoid arthritis and possibly multiple sclerosis and systemic lupus erythematosus.

Since the rejection of organ grafts is considered to be predominantly a cell-mediated immune phenomenon, a further area of usefulness of the compounds of this invention is in the prevention of transplant rejection.

The compounds of this invention can be administered intravenously, subcutaneously, intramuscularly, orally, rectally, or by aerosolization in the form of sterile implants for long action. They can be formulated in any of a number of pharmaceutical compositions and nontoxic carriers to this end.

The pharmaceutical compositions can be sterile, injectable suspensions or solutions, or solid, orally administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile, injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride, or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

PROCESS FOR THE SYNTHESIS OF THE COMPOUNDS OF THIS INVENTION

One of the preferred groups of compounds of the present invention are the carboxylic acids represented by formula II:

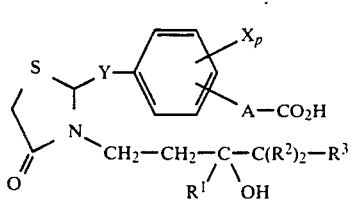

wherein A, X, Y, p, $R^1$, $R^2$, and $R^3$ are as previously defined. These acids are synthesized by a four-step process which will now be described.

STEP 1

An aldehyde of formula III:

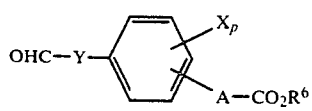

wherein A, X, p, and Y are as previously defined, and $R^6$ is straight chain lower alkyl (preferably methyl or ethyl) is condensed with a primary amine of formula IV:

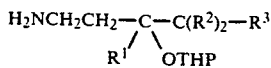

wherein $R^1$, $R^2$, and $R^3$ are as previously defined, and THP is the tetrahydro-2H-pyran-2-yl group. The product of this condensation is the imine of formula V:

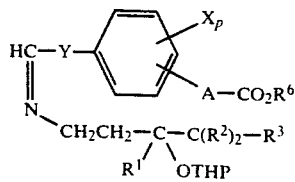

wherein all groups are as defined previously.

According to the preferred practice, aldehyde III is added dropwise to the amine IV while maintaining a temperature preferably at 0°-5° C. Anhydrous sodium sulfate or magnesium sulfate is then added and the mixture stirred at room temperature for a period of 0.5 to 4 hours. The solid is removed by filtration. The filtrate consists of the crude imine V which is used in the next step.

STEP 2

Mercaptoacetic acid is condensed with imine V to yield the thiazolidinone of formula VI:

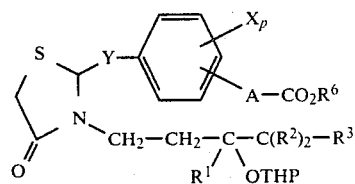

wherein all groups are as defined previously.

This condensation is most advantageously conducted by dissolving mercaptoacetic acid and imine V in a solvent such as benzene and toluene, and boiling the solution under reflux in a Dean-Stark or similar apparatus for the removal of the water formed in the condensation.

STEP 3

Thiazolidinone VI is treated with a trace of strong acid such as concentrated hydrochloric acid in a protic solvent, preferably methanol or ethanol, at room temperature for a period of 1 to 24 hours. This treatment hydrolyzes the protecting tetrahydropyranyl (THP) group and produces the thiazolidinone of formula VII:

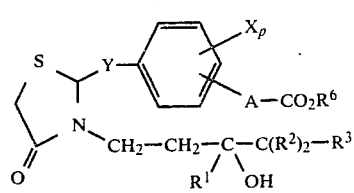

wherein all groups are as previously defined.

STEP 4

Thiazolidone ester VII is subjected to basic hydrolysis (dilute NaOH, LiOH, or KOH in methanol, ethanol, or tetrahydrofuran) at room temperature to remove the protecting ester function ($OR^6$) and produce the thiazolidinone carboxylic acid of formula II, one of the products of this invention.

DERIVATIZATION OF PRODUCTS OF FORMULA II FROM THE PRINCIPAL PROCESS

The principal process described in the preceeding sections produces carboxylic acids (see Formula II). To obtain carboxy salts, the acid products are dissolved in a solvent such as ethanol, methanol, glyme, and the like, and the solution treated with an appropriate alkali or alkaline earth hydroxide or alkoxide to yield the metal salt, or with an equivalent quantity of ammonia, amine, or quarternary ammonium hydroxide to yield the amine salt. In each instance, the salt either separates from the solution and may be separated by filtration, or, when the salt is soluble, it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine, or a quarternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane.

When the groups A and Y in aldehydes III are unsaturated (i.e., contain double bonds), the primary products of formula II derived from them will likewise be unsaturated; i.e., they will have double bonds in either A or Y. Such primary products can be hydrogenated over platinum or palladium catalysts to yield further saturated products of this invention of formula II wherein A and Y are saturated chains.

PREPARATION OF INTERMEDIATES

The aldehyde intermediates III which have the following general formula:

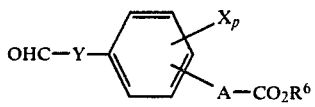

III wherein $R^6$, X, A, p, and Y are as described previously, are a broad group of compounds, some of which have been described in the chemical literature. No single general method of synthesis can be prescribed for these compounds; a variety of known organic reactions can be selected for their preparation, depending on the length and nature of chains A and Y and the orientation of these chains on the benzene ring (para or meta). The following examples are chosen to illustrate the procedures that are most useful in the preparation of the reagents III.

(a) Reagents III with Para Orientation

1. When $R^6$ is ethyl, X is hydrogen, A is $(CH_2)_o$ (a single bond), Y is $(CH_2)_3$, and A and Y are in the para orientation, the reagent III becomes ethyl 4-(4-oxobutyl)-benzoate (IX):

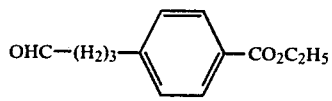

IX

In the preparation of IX, the dianion prepared by the action of lithium diisopropylamide on p-toluic acid is alkylated with 2-(2-bromoethyl)-1,3-dioxolane. The resulting 4-{3-[2-(1,3-dioxolanyl)]propyl}benzoic acid is esterified with ethyl iodide in the presence of potassium carbonate. Acid hydrolysis of the protecting cyclic acetal moiety gives the aldehyde reagent IX.

The use of 2-(3-bromopropyl)-1,3-dioxolane in the initial alkylation affords the higher homolog of IX in which Y is $(CH_2)_4$.

2. When $R^6$ is ethyl, X is hydrogen, A is $(CH_2)_o$, Y is $(CH_2)_4$, and A and Y are in the para orientation, the reagent III becomes ethyl 4-(5-oxopentyl)benzoate (X):

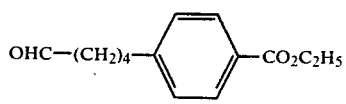

X

Note that X is the higher homolog of X mentioned in the preceding section 1.

In this alternate preparation of X, 4-bromobutylbenzene is acylated with acetyl chloride and aluminum chloride; the resulting acetophenone is oxidized with sodium hypobromite to the benzoic acid, and this compound is esterified with ethanol and mineral acid to afford ethyl 4-(4-bromobutyl)benzoate. This ester is treated with the anion prepared from methyl methylthiomethyl sulfoxide and a strong base such as sodium hydride. The resulting dimethyl mercaptal S-oxide is hydrolyzed with acid catalysis to the aldehyde reagent X.

The last two steps of this process are illustrated by the following scheme:

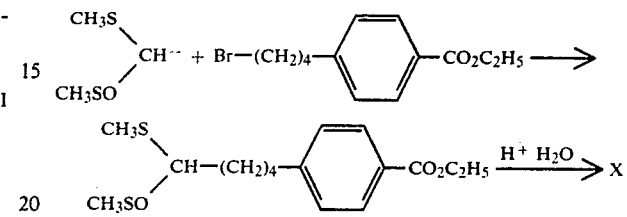

3. When $R^6$ is ethyl, X is hydrogen, A is vinylene (—CH=CH—), Y is $CH_2$, and A and Y are in the para orientation, the reagent III becomes ethyl p-(2-oxoethyl)-cinnamate XI:

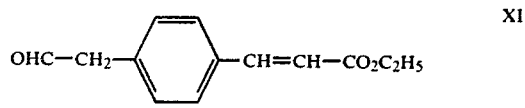

XI

In the preparation of XI, ethyl p-methylcinnamate is treated with N-bromosuccinimide in carbon tetrachloride to yield ethyl p-(bromoethyl)cinnamate. This ester is treated with the anion derived from methyl methylthiomethyl sulfoxide and sodium hydride. The resulting dimethyl mercaptal S-oxide is hydrolyzed with acid catalysis to the aldehyde reagent XI.

Note that the reagent XI is the functional equivalent of the reagent III wherein $R^6$ is ethyl, X is hydrogen, A is $(CH_2)_2$, Y is $CH_2$, and A and Y are in the para orientation (ethyl p-(2-oxoethyl)hydrocinnamate) XII:

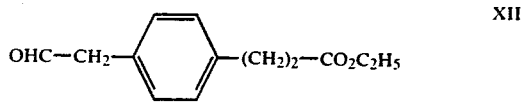

XII

This is because the product II derived from XI in which A is necessarily vinylene (—CH=CH—) can be hydrogenated to yield a product II wherein A is $(CH_2)_2$. This latter product is the same as would be obtained when aldehyde XII would be used in the principal synthesis.

(b) Reagents III with Meta Orientation

When $R^6$ is ethyl, X is hydrogen, A is $(CH_2)_o$, Y is —$CH_2CH=CH$—, and A and Y are in meta orientation, the reagent III becomes ethyl 3-(4-oxo-1-butenyl)-benzoate XIII:

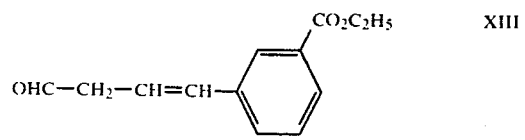

XIII

The preparation of XIII begins with the known methyl 3-(bromomethyl)benzoate. This halide is heated in xylene solution with triphenylphosphine to yield (3-methoxycarbonylbenzyl)triphenylphosphonium bromide. The phosphonium salt is converted to the ylide with sodium ethoxide in ethanol and the ylide caused to react with acetaldehyde to yield ethyl 3-(1-propenyl)-benzoate. [Note that the ethyl ester has been obtained as a result of transesterification with solvent ethanol.] The ester is heated with N-bromosuccinimide in carbon tetrachloride for an extended period to yield ethyl 3-(3-bromo-1-propenyl)benzoate. This compound is treated with the anion derived from methyl methylthiomethyl sulfoxide as described in previous examples. The resulting dimethyl mercaptal S-oxide is hydrolyzed with acid catalysis to the aldehyde reagent XIII.

Note that the reagent XIII is the functional equivalent of the reagent III wherein $R^6$ is ethyl, X is hydrogen, A is $(CH_2)_o$, Y is $(CH_2)_3$, and A and Y are in the meta orientation (ethyl 3-(4-oxobutyl)benzoate) XIV:

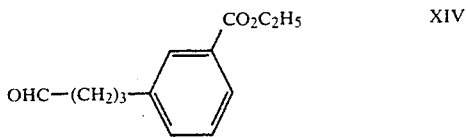

This is because the product II derived from XIII in which Y is necessarily $-CH_2-CH=CH-$ can be hydrogenated to yield a product II wherein Y is $(CH_2)_3$. This latter product is the same as would be obtained when aldehyde XIV would be used in the principal synthesis.

II The amine reagents of formula IV:

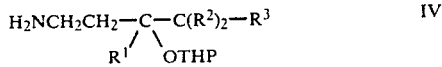

wherein $R^1$, $R^2$, $R^3$, and THP are as described previously are prepared by the following process.

Lithium diisopropylamide is made to react with acetonitrile in a suitable inert solvent such as tetrahydrofuran to give the anion $Li^+ \ ^-CH_2CN$. The anion is then added to aldehydes or ketones $R^1-CO-C(R^2)_2-R^3$. Some features of the reagents $R^1-CO-C(R^2)_2-R^3$ should be noted. These reagents are aldehydes when $R^1$ is hydrogen. When $R^3$ is joined to $R^1$ (when $R^1$ is methyl) or to CO with abstraction of hydrogen (when $R^1$ is hydrogen), these reagents are cyclic ketones such as cyclohexanone.

In any event, the anion addition provides alcohols:

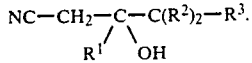

Treatment of the alcohols with dihydropyran in the presence of a suitable acid catalyst such as p-toluenesulfonic acid at room temperature gives the protected alcohols:

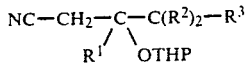

where THP is the tetrahydro-2H-pyran-2-yl group as explained previously.

The protected alcohols are reduced with lithium aluminum hydride in a suitable inert solvent such as tetrahydrofuran or ether to afford the amine reagents IV.

EXAMPLE 1

Preparation of 4-{3-[3-(3-Hydroxyoctyl)-4-oxo-2-thiazolidinyl]-propyl}benzoic Acid Step A: Preparation of Ethyl 4-(4-Oxobutyl)benzoate Step A-1: Preparation of Ethyl 4-{3-[2-(1,3-Dioxolanyl)]-propyl}benzoate n-Butyl lithium solution (2.29 M in hexane, 35 ml., 80 mmol.) is added to a stirred solution of di-i-propylamine (8.08 g., 80 mmol.) in anhydrous THF (tetrahydrofuran, 120 ml.) and HMPA (hexamethylphosphonamide, 10 ml.) under nitrogen atmosphere. Subsequent addition of a THF (20 ml.) solution of p-toluic acid (5.44 g., 40 mmol.) results in a deep greenish-brown solution. The deep-colored solution is stirred at 0° C. for 30 minutes before being treated with a THF (10 ml.) solution of 2-(2-bromoethyl)-1,3-dioxolane. The resulting mixture is stirred for 30 minutes, and then quenched with cold water. The organic phase is separated, the aqueous layer is acidified with hydrochloric acid (2 N), and then extracted with ether. The latter ethereal extraction is washed with water, dried over anhydrous magnesium sulfate, filtered, and concentrated to give a solid residue.

The solid residue is dissolved in DMF (dimethylformamide, 50 ml.) and then successively treated with potassium carbonate (69.1 g., 50 mmol.) and ethyl iodide (9.36 g., 60 mmol.). The resulting mixture is stirred at ambient temperature for 16 hours. Additional ethyl iodide (1 g.) is added to the reaction mixture, following by heating on a steam bath for 10 minutes. The reaction mixture is then allowed to cool to room temperature, quenched with cold water, and extracted with ether. The ethereal extract is washed successively with diluted hydrochloric acid and 5% sodium bicarbonate, dried over anhydrous magnesium sulfate, filtered, and evaporated to leave an oil residue. The residue is then fractionated to give ethyl benzoate (2 g., b.p. 55°–59° C. at 0.05 mmHg.), and the desired title compound (5.81 g., 22 mmol., 55%, b.p. 135°–140° C. at 0.05 mm.), pmr (CDCl$_3$) δ1.39 (3H, t, J=7 Hz), 1.76 (2H, m), 2.74 (2H, m), 3.90 (4H, m), 4.40 (2H, q, J=7 Hz), 4.89 (1H, t), 7.26 (2H, d, J=8 Hz), 8.0 (2H, d, J=8 Hz).

Step A-2: Preparation of Ethyl 4-(4-Oxobutyl)benzoate

A mixture of ethyl 4-{3-[3-(1,3-dioxolanyl)]-propyl}-benzoate (0.90 g., 3.4 mmol.), water (7 ml.), acetic acid (14 ml.) plus five drops of concentrated hydrochloric acid is stirred at 50°–65° C. for 4 hours. The reaction mixture is diluted with water and extracted with ether. The ethereal extract is then washed with water twice, 5% sodium bicarbonate solution three times till neutral, dried over anhydrous magnesium sulfate, and evaporated to give the desired title compound as a pale yellow oil, pmr (CDCl$_3$) δ 1.40 (3H, t, J=7 Hz), 1.7~3.0 (6H, m), 4.40 (2H, q, J=7 Hz), 7.25 (2H, d, J=8 Hz), 8.0 (2H, d, J=8 Hz), 9.80 (1H, m).

Step B: Preparation of 1-Amino-3-(tetrahydro-2H-pyran-2-yloxy)octane

Step B-1: Preparation of 3-Hydroxycaprylonitrile

A 1.9 M solution (21 ml. 40 millimole) of n-butyl lithium in hexane is added cautiously to a stirred solution of freshly distilled diisopropylamine (4.04 g., 40 millimole) in anhydrous tetrahydrofuran (60 ml.) maintained at 0° C. under a nitrogen atmosphere. The resulting solution is stirred at ambient temperature for 15 minutes, cooled to −78° C., and treated with a solution of anhydrous acetonitrile (1.64 g., 40 millimole) in anhydrous tetrahydrofuran (5 ml.). The resulting turbid suspension is stirred and maintained at −78° C. for 30 minutes and then treated with a solution of hexanal (4.0 g., 40 millimole) in anhydrous tetrahydrofuran (5 ml.). After attaining a clear, yellow reaction solution, cooling at −78° C. is maintained for an additional 15 minutes. The cold reaction solution is treated with 2 N hydrochloric acid (50 ml.) and extracted with ether (100 ml.). The organic extract is washed with water (50 ml.) and 5% aqueous bicarbonate (50 ml.), dried over magnesium sulfate, filtered and evaporated in vacuo, leaving the title compound as a pale yellow oil (5.2 g., 92%), pmr (CDCl$_3$) δ 0.97 (3H, t), 2.55 (2H, d), 3.10 (H, s) and 3.93 (H, bs).

Step B-2: Preparation of 3-(Tetrahydro-2H-pyran-2-yloxy)-caprylonitrile

A mixture of 3-hydroxycaprylonitrile (5.2 g., 36.8 millimole), dihydropyran (3.8 g., 45 millimole), and p-toluenesulfonic acid·hydrate (catalytic amount) is stirred at 25° C. for 16 hours, then diluted with ether (100 ml.). The resulting solution is washed with 5% aqueous sodium hydroxide (25 ml.) and water (2×25 ml.), dried over magnesium sulfate, and filtered. Evaporation of the filtrate in vacuo affords the title compound as a pale yellow oil (7.9 g., 95%), pmr (CDCl$_3$) δ 0.93 (3H, t), 2.54 (2H, q) and 4.68 (H, m).

Step B-3: Preparation of 1-Amino-3-(tetrahydro-2H-pyran-2-yloxy)octane

A solution of 3-(tetrahydro-2H-pyran-2-yloxy)-caprylonitrile (4.05 g., 18 millimole) in dry ether (10 ml.) is added dropwise to a stirred suspension of lithium aluminum hydride (0.76 g., 20 millimole) in dry ether (90 ml.) maintained under a nitrogen atmosphere. Upon completion of the addition, the reaction mixture is stirred and heated at reflux for 16 hours. After cooling to 25° C., the reaction mixture is treated successively with water (1 ml.), and 5% aqueous sodium hydroxide (3 ml.) added dropwise with caution, affording a fine suspension which is cooled to and maintained at 0°-5° C. for 30 minutes, and filtered. In vacuo evaporation of the solvent leaves the title compound as a pale yellow oil (3.95 g., 95%), pmr (CDCl$_3$) δ 0.88 (3H, t), 2.79 (2H, m) and 4.68 (H, bs).

Step C: Preparation of Ethyl 4-{3-[3-(3-Hydroxyoctyl)-4-oxo-2-thiazolidinyl]propyl}benzoate Ethyl 4-(4-oxobutyl)benzoate (4.63 g., 21 mmol.) is added dropwise to 1-amino-3-(tetrahydro-2H-pyran-2-yloxy)octane (4.82 g., 21 mmol.) at ambient temperature. The resulting mixture is stirred for 15 minutes before adding anhydrous sodium sulfate (4 g.), and then stirred for 1 hour. The solid is subsequently removed by filtration and washed with a small quantity of benzene. The combined filtrate and washings are diluted with benzene (70 ml.) and then treated with mercaptoacetic acid (1.93 g., 21 mmol.). The resulting solution is refluxed in a Dean-Stark apparatus for 3 hours. The reaction mixture is allowed to cool to room temperature, washed successively with dilute hydrochloric acid, 5% sodium bicarbonate, dried over anhydrous magnesium sulfate, and concentrated to give an oil residue. A methanol solution (50 ml.) of the oil residue is treated with concentrated hydrochloric acid (0.2 ml.) and then stirred at ambient temperature for 16 hours. The reaction mixture is diluted with cold water, followed by extraction with ether. The ethereal extract is washed with water, 5% sodium bicarbonate, dried over anhydrous magnesium sulfate, and filtered. Evaporation of the filtrate in vacuo provides an oil residue which is then applied to a silica gel column (300 g.) with chloroform. Elution with chloroform-methanol (100:1; v:v; 1950 ml.) provides impure material; further elution with the same eluant (450 ml.) gives the title compound as a pale yellow oil (2.80 g., 6.64mmol., 31%), pmr (CDCl$_3$) δ 0.90 (3H, t), 1.40 (3H, t), 3.53 (2H, s), 4.40 (2H, q), 4.70 (1H, m), 7.22 (2H, d), 8.0 (2H, d).

Step D: Preparation of 4-{3-[3-(3-Hydroxyoctyl)-4-oxo-2-thiazolidinyl]propyl}benzoic Acid Sodium hydroxide solution (5 N, 2.5 ml., 12.5 mmol.) is added dropwise to a stirred mixture of ethyl 4- 3-[3-(hydroxyoctyl)-4-oxo-2-thiazolidinyl]propyl benzoate (2.80 g., 6.64 mmol.) in aqueous mathanol (25 ml. methanol plus 5 ml. water) maintained at 0° C. The resulting mixture is allowed to warm to room temperature and stirred for 3 hours. Then, the reaction mixture is diluted with water, and extracted with ether. The aqueous phase is separated, acidified with 2 N hydrochloric acid (10 ml.), and extracted with ether. This ethereal extract is washed with water, dried over anhydrous magnesium sulfate, concentrated in vacuo to yield an oil residue. The oil residue is then applied to a silica gel column (75 g.) with chloroform. Elution with chloroform-acetic acid (25:1; v:v; 410 ml.) gives impure material. Continued elution with the same eluant (420 ml.) provides the desired title compound as a viscous pale yellow oil, ir (NaCl) 1700, 1665 cm$^{-1}$, pmr (CDCl$_3$) δ 0.92 (3H, t), 3.60 (2H, s), 4.72 (1H, m), 7.30 (2H, d), 8.08 (2H, d).

Anal. Calcd. for $C_{21}H_{31}ND_4S$: C,64.09; H,7.94; N,3.56; S,8.15. Found: C,63.93; H,7.70; N,3.20; S,8.04.

EXAMPLE 2

Preparation of 4-{3-[3-[2-(1-Hydroxycyclohexyl)ethyl]-4-oxo-2-thiazolidinyl]propyl}benzoic Acid Step A-1: Preparation of 2-(1-Hydroxycyclohexyl)acetonitrile n-Butyl lithium (1.6 M solution in n-hexane, 125 ml., 0.2 mol.) is added to a solution of di-i-propylamine (20.2 g., 0.2 mol.) in THF (280 ml.) at 0° C. under nitrogen atmosphere. The resulting mixture is then cooled to −78° C. (dry ice-isopropanol), followed by the addition of a THF (10 ml.) solution of acetonitrile (8.20 g., 0.2 mol.). The resulting mixture is stirred at −78° C. for 20 minutes, then treated with cyclohexanone (19.6 g., 0.2 mol.) and HMPA (15 ml.). Stirring is continued at −78° C. for 45 minutes before the reaction mixture is allowed to warm to room temperature. The reaction mixture is diluted with ether (100 ml.), quenched with water (200 ml.), and acidified with 3.5 N hydrochloric acid (140 ml.). The organic phase is separated, washed with water (200 ml.) and 5% sodium bicarbonate (100 ml.), dried over anhydrous magnesium sulfate, and filtered. Evaporation of the solvent in vacuo leaves the title compound as a pale yellow oil (23.6 g., 0.17 mol., 85%), pmr (CDCl$_3$) δ 1.64 (8H, bs), 2.54 (2H, s), 2.64 (1H, s).

Step A-2: Preparation of 2-[1-(Tetrahydro-2H-pyran-2-yl-oxy)cyclohexyl]acetonitrile P-Toluenesulfonic acid hydrate (0.1 g.) is added to a stirred mixture of 2-(1-hydroxycyclohexyl)acetonitrile (5.57 g., 40 mmol.) and dihydropyran (3.78 g., 45 mmol.). As soon as the reaction is initiated (indicated by the temperature rise of the reaction mixture) the reaction vessel is quickly chilled in a cold water bath and stirring continued for 1.5 hours. The reaction mixture is then diluted with ether, washed with 5% sodium bicarbonate and dried over anhydrous magnesium sulfate. Evaporation of the solvent in vacuo provides the title compound as a yellow oil (8.70 g., 39 mmol., 98%), pmr (CDCl$_3$) δ 2.63 (2H, s), 3.3~4.3 (2H, m), 4.87 (1H, m).

Step A-3: Preparation of 1-Amino-2-[1-(tetrahydro-2H-pyran-2-yloxy)cyclohexyl]ethane An ether (20 ml.) solution of 2-[1-(tetrahydro-2H-pyran-2-yloxy)cyclohexyl]acetonitrile (8.70 g., 39 mmol.) is added dropwise to a stirred suspension of lithium aluminum hydride (1.292 g., 34 mmol.) in ether (100 ml.). The resulting mixture is then refluxed for 16 hours. The reaction mixture is cooled to below 5° C., treated successively with water (1.3 ml.), 15% sodium hydroxide (1.3 ml.) and then water again (3.9 ml.). The resulting mixture is stirred at ambient temperature for 30 minutes and the precipitated solid is filtered off. The filtrate is concentrated in vacuo to yield the title compound as a pale yellow viscous oil (8.7 g., 38.2 mmol., 98%), pmr (CDCl$_3$) δ 2.35 (2H, s, exchangeable with D$_2$O), 2.6~3.0 (1H, m), 3.2~4.2 (3H, m), 4.74 (1H, m).

Step B: Preparation of Ethyl 4- 3-[3-[2-(1-Hydroxycyclohexyl)ethyl]-4-oxo-2-thiazolidinyl]propyl benzoate Ethyl 4-(4-oxobutyl)benzoate (4.15 g., 18.8 mmol.) is added dropwise to a stirred solution of 1-amino-2-[1-(tetrahydro-2H-pyran-2-yloxy)cyclohexyl]ethane in carbon tetrachloride (1 ml.) maintained at 25° C. The resulting mixture is stirred for 30 minutes before being treated with anhydrous sodium sulfate (4 g.). Stirring is continued for 2 hours. The solid is removed by filtration and washed with a small quantity of benzene. The combined filtrate and washings are diluted with benzene (70 ml.), treated with HSCH$_2$CO$_2$H (1.84 g., 20 mmol.) in one portion, and then refluxed in a Dean-Stark apparatus for 16 hours. The reaction mixture is allowed to cool to room temperature, subsequently washed with diluted hydrochloric acid and 5% sodium bicarbonate, dried over anhydrous magnesium sulfate, and filtered. Evaporation in vacuo affords an oil residue which is dissolved in methanol (50 ml.) plus concentrated hydrochloric acid (0.2 ml.). The resulting mixture is stirred at ambient temperature for 3 hours, diluted with water, and extracted with ether. The ethereal extract is washed with diluted sodium bicarbonate, dried over anhydrous magnesium sulfate, filtered, and concentrated to give an oil residue. The oil residue is then applied to a silica gel column (120 g.) with chloroform. Elution with chloroform-methanol (100:1; v:v; 630 ml.) gives impure material. Further elution with the same eluant (300 ml.) provides the title compound (2.5 g., 5.96 mmol., 32%) as a pale yellow oil, pmr (CDCl$_3$) δ 1.38 (3H, t), 3.50 (2H, s), 4.40 (2H, q), 4.72 (1H, m), 7.23 (2H, d), 8.00 (2H, d).

Step C: Preparation of 4-{3-[3-[2-(1-Hydroxycyclohexyl)-ethyl]-4-oxo-2-thiazolidinyl]propyl}benzoic Acid Sodium hydroxide solution (5 N, 2.5 ml., 12.5 mmol.) is added to a stirred mixture of ethyl 4-{3-[3-[2-(1-hydroxycyclohexyl)ethyl]-4-oxo-2-thiazolidinyl]-propyl}-benzoate (2.48 g., 5.91 mmol.), methanol (25 ml.) and water (5 ml.). The resulting mixture is stirred at ambient temperature for 16 hours. Then, it is diluted with water, acidified with diluted hydrochloric acid, and extracted with ether. The ethereal extract is washed with water, dried over anhydrous magnesium sulfate, and filtered. Upon cooling the filtrate, the title compound precipitates out as a white solid, which is collected by filtration (7.06 g., 2.57 mmol., 42%). The product is recrystallized from chloroform-ether, m.p. 147°–148° C., ir (KBr) 3320, 1700, 1650 cm$^{-1}$, pmr (CDCl$_3$) δ 3.54 (2H, s), 4.70 (1H, m), 7.22 (2H, d), 8.00 (2H, d).

Anal. Calcd. for C$_{21}$H$_{29}$NO$_4$S: C, 64.42; H, 7.47; N, 3.58.

Found: C, 63.97; H, 7.23; N, 3.40.

EXAMPLE 3

Preparation of 4-{3-[3-[2-(1-Hydroxycyclohexyl)ethyl]-1,4-dioxo-2-thiazolidinyl]propyl}benzoic Acid Sodium metaperiodate (0.75 g., 3.5 mmoles) is added to a cold (0°–5° C.) solution of 4-{3-[3-[2-(1-hydroxycyclohexyl)ethyl]-4-oxo-2-thiazolidinyl]propyl}benzoic acid (1.33 g., 3.4 mmoles) in methanol (20 ml.) and water (5 ml.). The resulting mixture is stirred without further cooling for 16 hours. The precipitated solid is then removed by filtration. The filtrate is diluted with water and extracted with chloroform. The organic extract is washed with brine, dried over sodium sulfate, and evaporated in vacuo to leave an oily residue which is chromatographed on silica gel (25 g.). Elution with 4% acetic acid in chloroform affords the title compound as a viscous, yellowish oil.

EXAMPLE 4

Preparation of 4-{3-[3-[2-(1-Hydroxycyclohexyl)ethyl]-1,1,4-trioxo-2-thiazolidinyl]propyl}benzoic Acid A mixture of 4-{-b 3-[3-[2-(1-hydroxycyclohexyl)-ethyl]-4-oxo-2-thiazolidinyl]propyl}benzoic acid (0.391 g., 1.0 mmol.), m-chloroperoxybenzoic acid (100%, 0.362 g., 2.1 mmol.), and chloroform (5 ml.) is refluxed for 30 minutes. The reaction mixture is evaporated in vacuo to give a solid residue which is applied to a silica gel column (18 g.) with chloroform. Elution with chloroform-acetic acid (25:1; v:v; 150 ml.) provides m-chlorobenzoic acid and impure material. Continued elution with the same eluant affords the title compound as a colorless viscous oil (0.273 g., 0.64 mmol., 64%), pmr (CDCl$_3$) δ 3.75 (2H, s), 4.60 (1H, m), 7.26 (2H, d), 8.00 (2H, d).

EXAMPLE 5

Preparation of 4-{3-[3-[2-(1-Hydroxycyclohexyl)ethyl]-4-oxo-2-thiazolidinyl]propyl}-3-chlorobenzoic Acid Step A: Preparation of Ethyl 3-Chloro-4-(4-oxobutyl)-benzoate This compound is prepared by the same series of reactions described in Example 1, Step A, for the preparation of ethyl 4-(4-oxobutyl)benzoate, except that in Step A-1, 3-chloro-4-methylbenzoic acid is substituted for p-toluic acid. There is thus obtained in Step A-1 of this example, ethyl 3-chloro-4-{3-[2-(1,3-dioxolanyl)]-propyl}-benzoate, b.p. 175°–178° C. (0.2 mm.); and in Step A-2, ethyl 3-chloro-4-(4-oxobutyl)benzoate.

Step B: Preparation of Ethyl 4-{3-[3-[2-(1-Hydroxycyclohexyl)ethyl]-4-oxo-2-thiazolidinyl]propyl}-3-chlorobenzoate This compound is prepared by the method described in Example 2, Step B, except that an equivalent quantity of ethyl 3-chloro-4-(4-oxobutyl)benzoate is substituted for the ethyl 4-(4-oxobutyl)benzoate of Example 2, Step B. The title compound is obtained as in viscous, brownish oil.

Step C: Preparation of 4-{3-[3-[2-(1-Hydroxycyclohexyl)-ethyl]-4-oxo-2-thiazolidinyl]propyl}-3-chlorobenzoic Acid The hydrolysis of the ester product of Step B above is carried out exactly analogously to the hydrolysis described in Example 2, Step C. The title compound after chromatography on silica gel with 2% methanol in chloroform elution is obtained as an extremely viscous, yellowish oil.

EXAMPLE 6

Preparation of 4-{3-[3-[2-(1-Hydroxycyclohexyl)ethyl]-4-oxo-2-thiazolidinyl]propyl}-2-chlorobenzoic Acid Step A: Preparation of Ethyl 2-chloro-4-(4-oxobutyl)benzoate This compound is prepared by the same series of reactions described in Example 1, Step A, for the preparation of ethyl 4-(4-oxobutyl)benzoate except that, in Step A-1, 2-chloro-4-methylbenzoic acid is substituted for p-toluic acid. There is thus obtained in Step A-1 of this example, ethyl 2-chloro-4-{3-[2-(1,3-dioxolanyl)]-propyl}benzoate, and in Step A-2, ethyl 2-chloro-4-(4-oxobutyl)-benzoate.

Step B: Preparation of Ethyl 4-{3-[3-2-(1-Hydroxycyclohexyl)ethyl]-4-oxo-2-thiazolidinyl]propyl}-2-chlorobenzoate This compound is prepared by the method described in Example 2, Step B, except that an equivalent quantity of ethyl 2-chloro-4-(4-oxobutyl)benzoate is substituted for the ethyl 4-(4-oxobutyl)benzoate of Example 2, Step B. The title compound is obtained as a viscous, orange oil.

Step C: Preparation of 4-{3-[3-[2-(1-Hydroxycyclohexyl)-ethyl]-4-oxo-2-thiazolidinyl]propyl}-2-chlorobenzoic Acid The hydrolysis of the ester product of Step B above is carried out exactly analogously to the hydrolysis described in Example 2, Step C. The title compound, after chromatography on silica gel with 2% methanol in chloroform elution, is obtained as an extremely viscous, yellowish oil.

EXAMPLE 7

Preparation of 4-{3-[3-[2-(1-Hydroxycyclohexyl)ethyl]-4-oxo-2-thiazolidinyl]propyl}-3-methylbenzoic Acid Step A: Preparation of Ethyl 3-Methyl-4-(4-oxobutyl)benzoate This compound is prepared by the same series of reactions described in Example 1, Step A, for the preparation of ethyl 4-(4-oxobutyl)benzoate except that in Step A-1, 3,4-dimethylbenzoic acid is substituted for p-toluic acid. There is thus obtained in Step A-1 of this example, ethyl 3-methyl-4-{3-[2-(1,3-dioxolanyl)]-propyl}benzoate, and in Step A-2, ethyl 3-methyl-4-(4-oxobutyl)benzoate.

Step B: Preparation of Ethyl 4-{3-[3-[2-(1-Hydroxycyclohexyl)ethyl]-4-oxo-2-thiazolidinyl]propyl}-3-methylbenzoate This compound is prepared by the method described in Example 2, Step B, except that an equivalent quantity of ethyl 3-methyl-4-(4-oxobutyl)benzoate is substituted for the ethyl 4-(4-oxobutyl)benzoate of Example 2, Step B. The title compound is obtained as a viscous, yellow oil.

Step C: Preparation of 4-{3-[3-[2-(1-Hydroxycyclohexyl)-ethyl]-4-oxo-2-thiazolidinyl]propyl}-3-methylbenzoic Acid The hydrolysis of the ester product of Step B above is carried out exactly analogously to the hydrolysis described in Example 2, Step C. The title compound, after chromatography on silica gel with 2% methanol in chloroform elution, is obtained as an extremely viscous, yellow oil.

EXAMPLE 8

Preparation of p-{3-[2-(1-Hydroxycyclohexyl)ethyl]-4-oxo-2-thiazolidinylmethyl}cinnamic Acid Step A-1: Preparation of Ethyl p-(Bromomethyl)cinnamate A mixture of ethyl p-methylcinnamate (19.0 g., 0.1 mole), N-bromosuccinimide (19.6 g., 0.11 mole), benzoyl peroxide (200 mg.), and carbon tetrachloride (200 ml.) is stirred and heated at reflux for 4 hours. The mixture is cooled and succinimide is removed by filtration. The filtrate is washed with 5% sodium bicarbonate solution and water and dried over sodium sulfate. The solvent is removed at reduced pressure and the residue distilled in vacuo to yield 14.8 g. (55%) of the title compound, b.p. 137°–140° C. (0.1 mm.).

Step A-2: Preparation of Ethyl p-(2-Oxoethyl)cinnamate

Methyl methylthiomethyl sulfoxide (12.4 g., 0.1 mole) is added dropwise during 30 minutes to a stirred suspension of sodium hydride (2.4 g., 0.1 mole) in tetrahydrofuran (100 ml.). Then, ethyl p-(bromomethyl)cinnamate (26.9 g., 0.1 mole) is added in one portion, and the mixture is stirred at 30° C. for 2 hours and at 45°–50° C. for 2 hours. The solvent is evaporated in vacuo. The residue is treated with water, and the oily product is taken up in ether and dried over sodium sulfate. Evaporation of the ether affords the dimethyl mercaptal S-oxide of the title aldehyde. This material is dissolved in 200 ml. of tetrahydrofuran with 5 ml. of 10% hydrochloric acid and the resulting solution is refluxed for 2 hours. The solvent is evaporated, and the residue is taken up in ether, washed with water, and dried over sodium sulfate. Evaporation of the solvent in vacuo affords the title aldehyde as a mobile oil which is used immediately in the next step.

Step B: Preparation of Ethyl p-{3-[2-(1-Hydroxycyclohexyl)ethyl]-4-oxo-2-thiazolidinylmethyl}cinnamate This compound is prepared by the method described in Example 2, Step B, except that an equivalent amount of ethyl p-(2-oxoethyl)cinnamate is substituted for ethyl 4-(4-oxobutyl)benzoate. The title compound is obtained as a viscous, yellow oil.

Step C: Preparation of p-{3-[2-(1-Hydroxycyclohexyl)ethyl]-4-oxo-2-thiazolidinylmethyl}cinnamic Acid This compound is prepared by the method described in Example 2, Step C, except that an equivalent quantity of the ester obtained in Step B above is subjected to hydrolysis. The title compound is purified by column chromatography on silica gel with 2% methanol in chloroform elution. It is obtained as a viscous, yellowish oil.

EXAMPLE 9

Preparation of
p-{3-[2-(1-Hydroxycyclohexyl)ethyl]-4-oxo-2-thiazolidinylmethyl}hydrocinnamic Acid p-{3-[2-(1-Hydroxycyclohexyl)ethyl]-4-oxo-2-thiazolidinylmethyl}cinnamic Acid (7.8 g., 0.02 mole) in ethanol (125 ml.) is hydrogenated over 2.5 g. of a 5% Pd on charcoal catalyst at 1 atmosphere pressure and 27° C. When the theoretical amount (0.02 mole) of hydrogen has been absorbed, the catalyst is filtered off, the solvent evaporated, and the residue chromatographed on silica gel with 4% methanol in chloroform as the eluant. The title compound is obtained as a colorless, viscous oil.

EXAMPLE 10

Preparation of
4-{4-[3-[2-(1-Hydroxycyclohexyl)ethyl]-4-oxo-2-thiazolidinyl]butyl}benzoic Acid Step A-1: Preparation of 4-(4-Bromobutyl)acetophenone A suspension of aluminum chloride (84 g., 0.63 mole) in a mixture of acetyl chloride (45 ml.) and carbon disulfide (300 ml.) is cooled in an ice bath and treated dropwise during 30 minutes with a mixture of 4-phenylbutyl bromide (128 g., 0.6 mole) and acetyl chloride (93 ml.). At the end of the addition, the temperature is 5°–10° C. The cooling bath is removed and stirring is continued for 2 hours.

The reaction mixture is poured in finaly ground ice (600 g.) and concentrated hydrochloric acid (60 ml.). The resulting oil is taken up in ether, washed with water, and dried over sodium sulfate. Solvents are evaporated, and the residual oil distilled at reduced pressure (14 mm.) to yield the title compound as a light yellow oil.

Step A-2: Preparation of 4-(4-Bromobutyl)benzoic Acid

A solution of sodium hydroxide (163.7 g., 4.092 moles) in water (1400 ml.) and dioxane (1000 ml.) is cooled to 15° C. and treated during 30 minutes with bromine (238.10 g., 1.488 moles) at 10°–15° C. Then 4-(4-bromobutyl)acetophenone (127 g., 0.496 mole) is added during 1 hour at 5°–10° C. Stirring is continued until the hypobromite is exhausted (about 2 hours).

The reaction solution is acidified with concentrated hydrochloric acid. The supernatant is decanted from a semi-solid which separates. This material is dissolved in ether, washed with water, and dried over magnesium sulfate. Evaporation of ether in vacuo affords the title acid which is purified by recrystallization from benzene and petroleum ether.

Step A-3: Preparation of Ethyl 4-(4-Bromobutyl)benzoate

A mixture of 4-(4-bromobutyl)benzoic acid (105.5 g., 0.41 mole), benzene (290 ml.), ethanol (60 ml.), and concentrated sulfuric acid (1.5 ml.) is heated at reflux under a Dean-Stark water separator until the evolution of water ceases (approximately 24 hours).

The cooled reaction solution is washed with water and dried over magnesium sulfate. The solvents are evaporated in vacuo, and the residual oil distilled at reduced pressure (0.1 mm.) to yield the title compound as a colorless, moderately viscous oil.

Step A-4: Preparation of Ethyl 4-(5-Oxopentyl)benzoate

Methyl methylthiomethyl sulfoxide (12.4 g., 0.1 mole) is added dropwise during 30 minutes to a stirred suspension of sodium hydride (2.4 g., 0.1 mole) in tetrahydrofuran (100 ml.). Then, ethyl 4-(4-bromobutyl)benzoate (28.5 g., 0.1 mole) is added in one portion, and the mixture is stirred at 30° C. for 2 hours and at 45°–50° C. for 18 hours. The solvent is evaporated in vacuo. The residue is treated with water, and the oily product is taken up in ether and dried over sodium sulfate. Evaporation of the ether affords the dimethyl mercaptal S-oxide of the title aldehyde. This material is dissolved in 200 ml. of tetrahydrofuran with 5 ml. of 10% hydrochloric acid, and the solution refluxed 3 hours. The solvent is evaporated; and the residue is taken up in ether, washed with water, and dried over sodium sulfate. Evaporation of the solvent in vacuo affords the title aldehyde as a mobile oil.

Step B: Preparation of Ethyl 4-{4-[3-[2-(1-Hydroxycyclohxyl)ethyl]-4-oxo-2-thiazolidinyl]butyl}benzoate This compound is prepared by the method described in Example 2, Step B, except that an equivalent quantity of ethyl 4-(5-oxopentyl)benzoate is substituted for ethyl 4-(4-oxobutyl)benzoate. The title compound is obtained as a viscous, yellow oil.

Step C: Preparation of 4-{4-[3-[2-(1-Hydroxycyclohexyl)-ethyl]-4-oxo-2-thiazolidinyl]butyl}benzoic Acid This compound is prepared by the method described in Example 2, Step C, except that an equivalent quantity of the ester of Step B above is subjected to hydrolysis. The title compound is purified by column chromatography on silica gel with 2% methanol in chloroform elution. It is obtained as a viscous, yellowish oil.

EXAMPLE 11

Preparation of
3-{3-[3-[2-(1-Hydroxycyclohexyl)ethyl]-4-oxo-2-thiazolidinyl]propenyl}benzoic Acid Step A-1: Preparation of Ethyl 3-(1-Propenyl)benzoate (3-Methoxycarbonylbenzyl)triphenylphosphonium bromide (54.1 g., 0.11 mole) is suspended with stirring in a mixture of acetaldehyde (5.8 g., 0.132 mole) and ethanol (250 ml.). A solution of sodium (2.5 g., 0.11 mole) in ethanol (300 ml.) is added dropwise during 30 minutes. The reaction mixture is stirred an additional 4 hours at room temperature and then concentrated to about ¼ volume at reduced pressure. Water (150 ml.) is added to the residue, and the oily product taken up in ether and dried over magnesium sulfate. Ether is evaporated. The residue is treated with 100 ml. of petroleum ether. Insoluble triphenylphosphine oxide is filtered off, and the filtrate distilled in vacuo to yield 14.0 g. (72%) of ethyl 3-(1-propenyl)benzoate, b.p. 85°–87° C. (0.1 mm.). Note that the product is an ethyl ester as a result of transesterification with solvent ethanol during the reaction.

Step A-2: Preparation of Ethyl 3-(3-Bromo-1-propenyl)benzoate

A mixture of ethyl 3-(1-propenyl)benzoate (14.0 g., 0.074 mole), N-bromosuccinimide (14.9 g., 0.084 mole), benzoyl peroxide (150 mg.), and carbon tetrachloride (75 ml.) is stirred and heated at reflux for 46 hours. The mixture is cooled. Solids are filtered off, and the filtrate is washed with water and dried over magnesium sulfate. The solvent is evaporated, and the residual oil distilled to yield 10.2 g. (51%) of ethyl 3-(3-bromo-1-propenyl)-benzoate, b.p. 129°–131° C. (0.05 mm.).

Step A-3: Preparation of Ethyl 3-(4-Oxo-1-butenyl)benzoate

This compound is prepared by the method described in Example 8, Step A-2, except that an equivalent amount of ethyl 3-(3-bromo-1-propenyl)benzoate is substituted for ethyl p-(bromomethyl)cinnamate.

Step B: Preparation of Ethyl 3-{3-[3-[2-(1-Hydroxycyclohexyl)ethyl]-4-oxo-2-thiazolidinyl]propenyl}benzoate This compound is prepared by the method described in Example 2, Step B, except that an equivalent amount of ethyl 3-(4-oxo-1-butenyl)benzoate is substituted for ethyl 4-(4-oxobutyl)benzoate. The title compound is obtained as a viscous, yellow oil.

Step C: Preparation of 3-{3-[3-[2-(1-Hydroxycyclohexyl)-ethyl]4-oxo-2-thiazolidinyl]propenyl}benzoic Acid This compound is prepared by the method described in Example 2, Step C, except that an equivalent quantity of the ester obtained in Step B is subjected to hydrolysis. The title compound is obtained as a viscous, yellow oil after purification by chromatography on silica gel with 2% methanol in chloroform elution.

EXAMPLE 12

Preparation of 3-{3-[3-[2-(1-Hydroxycyclohexyl)ethyl]-4-oxo-2-thiazolidinyl]propyl}benzoic Acid 3-{3-[3-[2-(1-Hydroxycyclohexyl)ethyl]-4-oxo-2-thiazolidinyl]propenyl}benzoic acid (7.8 g., 0.02 mole) (the compound of Example 11) in ethanol (125 ml.) is hydrogenated over 2.5 g. of a 5% Pd on charcoal catalyst at 1 atmosphere pressure and 27° C. When the theoretical amount (0.02 mole) of hydrogen has been absorbed, the catalyst is filtered off, the solvent evaporated, and the residue chromatographed on silica gel with 4% methanol in chloroform as the eluant. The title compound is obtained as a colorless, viscous oil.

EXAMPLE 13

Preparation of 4-{3-[3-(3-Hydroxy-3-methyloctyl)-4-oxo-2-thiazolidinyl]propyl}benzoic Acid This compound is prepared by the method described in Example 2, except that an equivalent quantity of 2-heptanone is substituted for the cyclohexanone employed in Example 2, Step A-1. There are thus obtained in the corresponding steps of this example:
(A-1) 3-hydroxy-3-methylcaprylonitrile;
(A-2) 3-(tetrahydro-2H-pyran-2-yloxy)-3-methylcaprylonitrile;
(A-3) 1-amino-3-(tetrahydro-2H-pyran-2-yloxy)-3-methyloctane;
(B) ethyl 4-{3-[3-(3-hydroxy-3-methyloctyl)-4-oxo-2-thiazolidinyl]propyl}benzoate; and
(C) 4-{3-[3-(3-hydroxy-3-methyloctyl)-4-oxo-2-thiazolidinyl]-propyl}benzoic acid.

EXAMPLE 14

Preparation of 4-{3-[3-(3-Hydroxy-4,4-dimethyloctyl)-4-oxo-2-thiazolidinyl]propyl}benzoic Acid This compound is prepared by the methods described in Example 1, Steps A through D, except that in Step B-1, an equivalent amount of 2,2-dimethylhexanal is substituted for the hexanal of Example 1, Step B-1. There are thus obtained successively in this example:
(Step B-1) 3-hydroxy-4,4-dimethylcaprylonitrile;
(B-2) 3-(tetrahydro-2H-pyran-2-yloxy)-4,4-dimethylcaprylonitrile;
(B-3) 1-amino-3-(tetrahydro-2H-pyran-2-yloxy)-4,4-dimethyloctane;
(C) ethyl 4-{3-[3-(3-hydroxy-4,4-dimethyloctyl)-4-oxo-2-thiazolidinyl]propyl}benzoate; and
(D) 4-{3-[3-(3-hydroxy-4,4-dimethyloctyl)-4-oxo-2-thiazolidinyl]propyl}benzoic acid.

EXAMPLE 15

Preparation of 4-{3-[3-(3-Hydroxydecyl)-4-oxo-2-thiazolidinyl]-propyl}benzoic Acid This compound is prepared by the methods described in Example 1, Steps A through D, except that in Step B-1, an equivalent amount of octanal is substituted for the hexanal of Example 1, Step B-1. There are thus obtained successively in this example:
(Step B-1) 3-hydroxydecanonitrile;
(B-2) 3-(tetrahydro-2H-pyran-2-yloxy)decanonitrile;
(B-3) 1-amino-3-(tetrahydro-2H-pyran-2-yloxy)decane;
(C) ethyl 4-{3-[3-(3-hydroxydecyl)-4-oxo-2-thiazolidinyl]-propyl}benzoate; and
(D) 4-{3-[3-(3-hydroxydecyl)-4-oxo-2-thiazolidinyl]-propyl}-benzoic acid.

EXAMPLE 16

Preparation of 4-{3-[3-(3-Hydroxy-7-octenyl)-4-oxo-2-thiazolidinyl]-propyl}benzoic Acid This compound is prepared by the methods described in Example 1, Steps A through D, except that in Step B-1, an equivalent amount of 5-hexenal is substituted for the hexanal of Example 1, Step B-1. There are thus obtained successively in this example:
(Step B-1) 3-hydroxy-7-octenonitrile;
(B-2) 3-(tetrahydro-2H-pyran-2-yloxy)-7-octenonitrile;
(B-3) 1-amino-3-(tetrahydro-2H-pyran-2-yloxy)-7-octene;
(C) ethyl 4-{3-[3-(3-hydroxy-7-octenyl)-4-oxo-2-thiazolidinyl]propyl}benzoate; and
(D) 4-{3-[3-(3-hydroxy-7-octenyl)-4-oxo-2-thiazolidinyl]-propyl}benzoic acid.

EXAMPLE 17

Preparation of 4-{3-[3-(3-Hydroxy-8,8,8-trifluorooctyl)-4-oxo-2-thiazolidinyl]propyl}benzoic Acid This compound is prepared by the methods described in Example 1, Steps A through D, except that in Step B-1, an equivalent amount of 6,6,6-trifluorohexanal is substituted for the hexanal of Example 1, Step B-1. There are thus obtained successively in this example:
(Step B-1) 3-hydroxy-8,8,8-trifluorocaprylonitrile;
(B-2) 3-(tetrahydro-2H-pyran-2-yloxy)-8,8,8-trifluorocaprylonitrile;
(B-3) 1-amino-3-(tetrahydro-2H-pyran-2-yloxy)-8,8,8-trifluorooctane;
(C) ethyl 4-{3-[3-(3-hydroxy-8,8,8-trifluorooctyl)-4-oxo-2-thiazolidinyl]propyl}benzoate; and
(D) 4-{3-[3-(3-hydroxy-8,8,8-trifluorooctyl)-4-oxo-2-thiazolidinyl]propyl}benzoic acid.

EXAMPLE 18

Preparation of
4-{3-[3-(3-Hydroxy-4-propoxybutyl)-4-oxo-2-thiazolidinyl]propyl}benzoic Acid This compound is prepared by the methods described in Example 1, Steps A through D, except that in Step B-1, an equivalent quantity of propoxyacetaldehyde is substituted for the hexanal of Example 1, Step B-1). There are thus obtained successively in this example:
(Step B-1) 3-hydroxy-4-propoxybutyronitrile;
(B-2) 3-(tetrahydro-2H-pyran-2-yloxy)-4-propoxybutyronitrile;
(B-3) 1-amino-3-(tetrahydro-2H-pyran-2-yloxy)-4-propoxybutane;
(C) ethyl 4-{3-[3-(3-hydroxy-4-propoxybutyl)-4-oxo-2-thiazolidinyl]propyl}benzoate; and
(D) 4-{3-[3-(3-hydroxy-4-propoxybutyl)-4-oxo-2-thiazolidinyl]propyl}benzoic acid.

EXAMPLE 19

Preparation of
4-{3-[3-[2-(1-Hydroxycyclopentyl)ethyl]-4-oxo-2-thiazolidinyl]propyl}benzoic Acid This compound is prepared by the method described in Example 2, except that an equivalent quantity of cyclopentanone is substituted for the cyclohexanone employed in Example 2, Step A-1. There are thus obtained in the corresponding steps of this example:
(Step A-1) 2-(1-hydroxycyclopentyl)acetonitrile;
(A-2) 2-[1-(tetrahydro-2H-pyran-2-yloxy)cyclopentyl]acetonitrile;
(A-3) 1-amino-2-[1-(tetrahydro-2H-pyran-2-yloxy)cyclopentyl]ethane;
(B) ethyl 4-{3-[3-[2-(1-hydroxycyclopentyl)ethyl]-4-oxo-2-thiazolidinyl]propyl}benzoate; and
(C) 4-{3-[3-[2-(1-hydroxycyclopentyl)ethyl]-4-oxo-2-thiazolidinyl]propyl}benzoic acid.

EXAMPLE 20

Preparation of
4-{3-[3-[2-(1-Hydroxycyclooctyl)ethyl]-4-oxo-2-thiazolidinyl]propyl}benzoic Acid This compound is prepared by the method described in Example 2, except that an equivalent quantity of cyclooctanone is substituted for the cyclohexanone employed in Example 2, Step A-1. There are thus obtained in the corresponding steps of this example:
(Step A-1) 2-(1-hydroxycyclooctyl)acetonitrile;
(A-2) 2-[1-(tetrahydro-2H-pyran-2-yloxy)cyclooctyl]acetonitrile;
(A-3) 1-amino-2-[1-(tetrahydro-2H-pyran-2-yloxy)cyclooctyl]ethane;
(B) ethyl 4-{3-[3-[2-(1-hydroxycyclooctyl)ethyl]-4-oxo-2-thiazolidinyl]propyl}benzoate; and
(C) 4-}3-[3-[2-(1-hydroxycyclooctyl)ethyl]-4-oxo-2-thiazolidinyl]propyl}benzoic acid.

EXAMPLE 21

Preparation of Methyl
4-{3-[3-[2-(1-Hydroxycyclohexyl)-ethyl]-4-oxo-2-thiazolidinyl]propyl}benzoate A solution of diazomethane (approximately 2.5 g., 0.06 mole) in ether (100 ml.) is mixed with a solution of 4-{3-[3-[2-(1-hydroxycyclohexyl)ethyl]-4-oxo-2-thiazolidinyl]propyl}benzoic acid (11.7 g., 0.03 mole) in ether (100 ml.). The resulting solution is allowed to stand at room temperature for 6 hours. Acetic acid is then added to destroy the excess diazomethane, and the solution is washed with dilute sodium bicarbonate solution and dried over sodium sulfate. Evaporation of volatile materials in vacuo yields the title compound as a nearly colorless, viscous oil.

EXAMPLE 22

Capsule Formulation

| | |
|---|---|
| 4-{3-[3-[2-(1-Hydroxycyclohexyl)ethyl]-4-oxo-2-thiazolidinyl]propyl}benzoic acid | 50 g. |
| Stearic acid (U.S.P. triple pressure) | 125 g. |
| Pluronic F-68 | 7.5 g. |
| Corn Starch | 125 g. |

The stearic acid and pluronic are united in a vessel and melted using a water bath at 60° to 65° C. The heating is discontinued and the 4-{3-[3-[2-(1-hydroxycyclohexyl)ethyl]-4-oxo-2-thiazolidinyl]propyl}benzoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 4-{3-[3-[2-(1-hydroxycyclohexyl)ethyl]-4-oxo-2-thiazolidinyl]propyl}benzoic acid per capsule.

EXAMPLE 23

Parenteral Formulation of a Multidose Solution for Intramuscular and Intravenous Use

| | |
|---|---|
| 4-{3-[3-[2-(1-Hydroxycyclohexyl)ethyl]-4-oxo-2-thiazolidinyl]propyl}benzoic acid | 1 g. |
| Tris-(hydroxymethyl)aminomethane (Reagent Grade THAM) | q.s. to adjust solution to pH 7.4 |
| Sodium Chloride (U.S.P.) | q.s. to yield isotonic solution |
| Methylparaben | 10 mg. |
| Polyparaben | 1 mg. |
| Distilled water (pyrogen-free) | q.s. to 10 ml. |

The 4-{3-[3-[2-(1-Hydroxycyclohexyl)ethyl]-4-oxo-2-thiazolidinyl]propyl}benzoic acid suspended in about 6 ml. of the water is treated with tris-(hydroxymethyl)-aminomethane with stirring until the pH reaches 7.4. The methylparaben and propylparaben are added with stirring and sufficient sodium chloride is added to produce an isotonic solution. After water is added to bring the final volume to 10 ml., the solution is sterilized by membrane filtration and placed in a vial by an aseptic technique. The solution contains the THAM salt of 4{3-[3-[2-(1-hydroxycyclohexyl)ethyl]-4-oxo-2-thiazolidinyl]propyl}benzoic acid equivalent to 100 mg./ml. of the free acid.

EXAMPLE 24

Preparation of Suppositories

| | |
|---|---|
| 4-{3-[3-[2-(1-Hydroxycyclohexyl)ethyl]-4-oxo-2-thiazolidinyl]propyl}benzoic acid | 200 g. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 g. |
| Sodium chloride, microfine | 52.5 g. |
| Polyethylene glycol 6000 | 128 g. |

| | |
|---|---|
| -continued | |
| Polyethylene glycol 4000 | 1269 g. |

The polyethylene glycol 4000 and polyethylene glycol 6000 are placed in a vessel surrounded by a water bath at such a temperature as required to maintain the melted contents at 60° to 65° C. To the melt is added the butylated hydroxyanisole and butylated hydroxytoluene with stirring. Then the ethylenediamine tetraacetic acid microfine sodium chloride are added to and dispersed in the mixture. The 4-{3-[3-[2-(1-Hydroxycyclohexyl)ethyl]-4-oxo-2-thiazolidinyl]propyl}benzoic acid is then added and dispersed into the mixture. Finally, the temperature is lowered to 55° to 60° C. and the glycerine is added and dispersed.

While maintaining the temperature of 55° to 60° C. and continuous mixing, the melt is dispersed into plastic suppository cavities of a conventional suppository cold-molding device. The suppositories thus prepared contain a total of 1.7778 g. of contents of which 200 mg. are 4-{3-[3-[2-(1-Hydroxycyclohexyl)ethyl]-4-oxo-2-thiazolidinyl]propyl}benzoic acid.

We claim:

1. The compound having the formula:

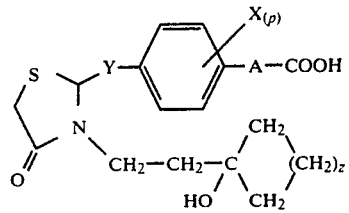

wherein
A is vinylene or $(CH_2)_m$ where m is 0 or 2;
Y is $CH_2CH=CH_2$ when m is 0, or Y is $CH_2$ when A is vinylene or ethylene;
X is hydrogen, halogen, or lower alkyl;
p is 1 or 2; and
z is an integer of 2 to 6.

2. The compound of claim 1 wherein A is vinylene and Y is —$CH_2$—.

3. p-{3-[2-(1-Hydroxycyclohexyl)ethyl]-4-oxo-2-thiazolidinylmethyl}cinnamic acid, the compound of claim 2 where X is hydrogen and z is 3.

4. The compound of claim 1 wherein A is $(CH_2)_2$ and Y is —$CH_2$—.

5. p-{3-[2-(1-Hydroxycyclohexyl)ethyl]-4-oxo-2-thiazolidinylmethyl}hydrocinnamic acid, the compound of claim 1 where X is hydrogen and z is 3.

6. The compound of claim 1 wherein A is $(CH_2)_o$ and Y is —$CH_2CH=CH$—.

7. 3-{3-[3-[2-(1-Hydroxycyclohexyl)ethyl]-4-oxo-2-thiazolidinyl]propenyl}benzoic acid, the compound of claim 6 where X is hydrogen and z is 3.

* * * * *